United States Patent
Regnat et al.

[11] Patent Number: 5,874,642
[45] Date of Patent: Feb. 23, 1999

[54] BIS ETHERS CONTAINING A 2,2'-BIARYL RADICAL AND A PROCESS FOR THEIR PREPARATION

[75] Inventors: Dieter Regnat, Eppstein; Hans-Jerg Kleiner, Kronberg; Helmut Bahrmann, Hamminkeln, all of Germany

[73] Assignee: Hoechst Aktiengesellschaft, Germany

[21] Appl. No.: 879,728

[22] Filed: Jun. 20, 1997

[30] Foreign Application Priority Data

Jun. 24, 1996 [DE] Germany .................. 196 25 167.2

[51] Int. Cl.$^6$ .................................................. C07C 43/03
[52] U.S. Cl. .................... 568/660; 585/400; 564/305
[58] Field of Search .......................... 568/660; 585/400; 564/305

[56] References Cited

U.S. PATENT DOCUMENTS

| 3,527,809 | 9/1970 | Pruett et al. | 260/604 |
| 3,917,661 | 11/1975 | Pruett et al. | 260/410.9 R |

FOREIGN PATENT DOCUMENTS

| 518 241 | 6/1992 | European Pat. Off. . |
| 1793069 | 6/1990 | Germany . |

OTHER PUBLICATIONS

T.N. Sorrell, "3,3'-Disubstituted 2,2'-biphenols: Synthesis of Nonplanar, Tetradentate Chelating Ligands" Journal of Organic Chemistry, Bd. 50, Nr. 26, 27, pp. 5764–5769, Dec. 1985.

J. Van Alphen, "Dimorphism of Tetranitrodiphenyl Derivatives", Recueil Des Travaux Chimiques Des Pays–Bas, Bd. Li, Nr. 5, pp. 453–459, May 15, 1932.

*Primary Examiner*—Shailendra Kumar
*Assistant Examiner*—Sreeni Padmanabhan
*Attorney, Agent, or Firm*—Connolly & Hutz

[57] ABSTRACT

The present invention relates to compounds of the formula (I)

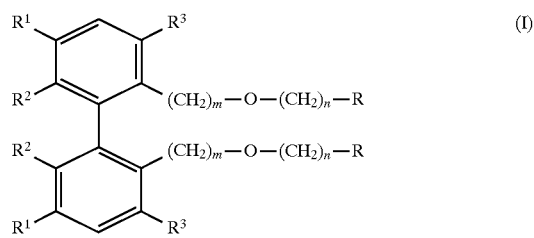

in which $R^1$, $R^2$ and $R^3$ are identical or different and, independently of one another, are hydrogen, an alkyl or alkoxy group having 1 to 4 carbon atoms, an alkenyl group having 2 to 4 carbon atoms, or $R^1$ and $R^2$ including the respective carbon atoms bound to them form a ring containing 6 carbon atoms, m and n independently of one another are 0 or 1 and (m+n) is 1 or 2, and R is an unsubstituted phenyl or naphthyl radical, or a phenyl or naphthyl radical substituted by an alkyl group having 1 to 4 carbon atoms or an amino or dialkylamino group containing a total of 2 to 8 carbon atoms, and to a process for their preparation.

19 Claims, No Drawings

BIS ETHERS CONTAINING A 2,2'-BIARYL RADICAL AND A PROCESS FOR THEIR PREPARATION

Owing to their chemical properties, aldehydes are an important group of organic compounds. They may be converted, for example, by the aldol reaction with themselves or another C—H acidic compound (methylene component) into the corresponding aldols or, after dehydration of the aldol, into the corresponding unsaturated condensation products. In addition, aldehydes may be oxidized to the corresponding carboxylic acids or may be reduced to the corresponding alcohols. By reacting aldehydes with ammonia or amines, imines or Schiff's bases may be obtained, which, by reaction with hydrogen, give the corresponding amines.

Aldehydes are obtained on an industrial scale by the hydroformylation of olefinic compounds. As a result of the reaction of the carbon-carbon double bond with carbon monoxide and hydrogen, mixtures of linear and branched aldehydes form, as the reaction equation below shows diagrammatically with reference to a terminal olefin.

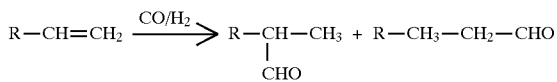

The mixtures are produced with variable composition, depending on the reaction conditions. In many cases, mixtures having the highest possible proportion of linear aldehydes and the lowest possible proportion of branched aldehydes are desired. In addition to the reaction conditions such as pressure and temperature, the hydroformylation catalyst used exerts a decisive influence on the course of the reaction and on the composition of the reaction mixture.

In the hydroformylation of olefins, rhodium catalysts which contain phosphorus-containing ligands have proved to be particularly useful as hydroformylation catalyst. Suitable phosphorus-containing ligands are phosphines or phosphites. DE 17 93 069 describes a hydroformylation process of this type.

However, it is a disadvantage that the phosphites and, in particular, the phosphines are unstable with respect to oxygen and sulfur and are oxidized even by very low amounts of oxygen and/or sulfur. This forms phosphates, thiophosphates, phosphine oxides and/or phosphine sulfides.

The oxygen passes into the reaction primarily via the olefin used as starting material, whereas the sulfur is supplied to the reaction via the synthesis gas, in the form of sulfur-containing compounds, for example as $H_2S$.

Oxygen and/or sulfur have harmful effects even in very low amounts, since the catalyst, after the hydroformylation has been carried out, is customarily separated off from the reaction product, for example by distillation, and reused in the hydroformylation stage, where it again comes into contact with the oxygen resulting from the starting olefin and with the sulfur or the sulfur-containing compounds supplied with the synthesis gas. As a consequence thereof, further amounts of phosphite or phosphine are reacted with oxygen and/or sulfur.

The resulting phosphates, thiophosphates, phosphine oxides and phosphine sulfides no longer function as complex-forming ligands and are thus no longer catalytically active. In addition, sulfur-containing compounds frequently impair catalytic processes and act as catalyst poisons.

The phosphates, thiophosphates, phosphine oxides and phosphine sulfides formed are undesirable in the hydroformylation and must therefore be separated off. Both the separation and the work-up of the still-active catalyst proves to be difficult and requires extensive use of equipment.

Although the phosphites are somewhat less sensitive to oxygen and/or sulfur than the phosphines, they are however sensitive to water and hydrolyze even under the influence of small to very small amounts of moisture. Small amounts of water pass into the reaction via the olefin used and the synthesis gas. Owing to the recycling of the catalyst containing the phosphites, they come into contact repeatedly with the water originating from the olefin and synthesis gas, which means that the hydrolysis progresses and more and more phosphite is hydrolytically cleaved. The hydrolysis products of the phosphites no longer act as complexing agent and are also no longer catalytically active.

In view of the described disadvantages with the use of phosphites and phosphines, there is a need to prepare substances which are insensitive to oxygen and/or sulfur and which also do not hydrolzye under the conditions of the hydroformylation. In addition, they should have complexing properties, they should not decrease the activity of the hydroformylation catalyst or the hydroformylation catalyst system, and should ensure that even in the case of relatively long service, there is no deactivation of the hydroformylation catalyst or the hydroformylation catalyst system.

This object is achieved by compounds of the formula (I)

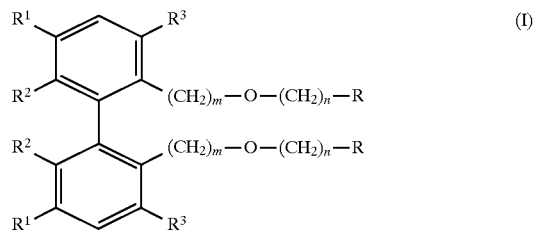

in which $R^1$, $R^2$ and $R^3$ are identical or different and, independently of one another, are hydrogen, an alkyl or alkoxy group having 1 to 4 carbon atoms, an alkenyl group having 2 to 4 carbon atoms, or $R^1$ and $R^2$ including the respective carbon atoms bound to them form a ring containing 6 carbon atoms, m and n independently of one another are 0 or 1 and (m+n) is 1 or 2, and R is a phenyl or naphthyl radical which is unsubstituted or substituted by an alkyl group having 1 to 4 carbon atoms or an amino or dialkylamino group containing a total of 2 to 8 carbon atoms.

Compounds which are of interest are those of the formula (I) in which $R^1$, $R^2$ and $R^3$ are identical or different and, independently of one another, are hydrogen, an alkyl or alkoxy group having 1 to 2 carbon atoms or $R^1$ and $R^2$ including the respective carbon atoms bound to them form a ring containing 6 carbon atoms.

The bridge resulting from the combination $R^1$ and $R^2$ which effects the ring closure and contains 4 carbon atoms is saturated or is monounsaturated or polyunsaturated, in particular unsaturated.

In the compounds of the formula (I), in particular m=1 and n=0, or m=1 and n=1.

R is a phenyl radical which is unsubstituted or substituted by an alkyl group having 1 to 4 carbon atoms, in particular a phenyl radical which is unsubstituted or substituted by an alkyl group having 1 to 2 carbon atoms, preferably a phenyl radical.

Compounds of particular interest are those which correspond to the formula (II) or (III),

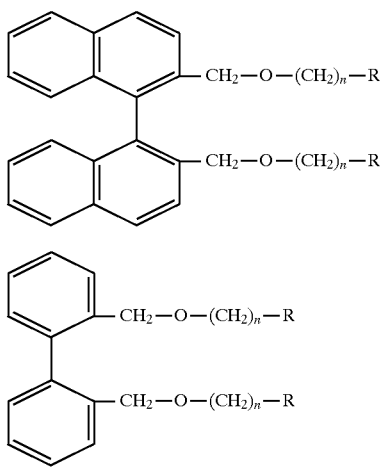

(II)

(III)

in which n and R have the meaning mentioned above.

The present invention further relates to a process for preparing the compounds of the formula (I), (II) and (III) respectively. The process comprises reacting a compound of the formula (IV)

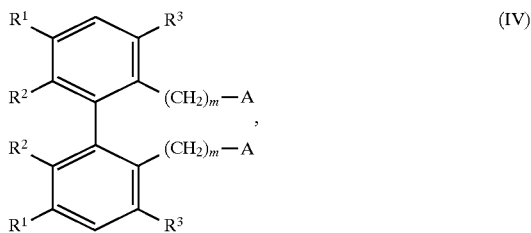

(IV)

in which $R^1$, $R^2$, $R^3$ and m have the meanings mentioned in formula (I) and A is OH or a leaving group Z, where Z is Cl, Br, I or a $R^4OSO_2$ group and $R^4$ is a $CH_3$, phenyl, tolyl or trialkylammonium radical having 1 to 4 carbon atoms per alkyl radical, with a compound of the formula (V)

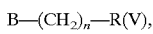B—$(CH_2)_n$—R(V), in which R and n have the meaning mentioned in formula (I) and B is the abovementioned leaving group Z if A is OH, or B is OH if A is the leaving group Z, in a molar ratio of 1:(2 to 2.2) in the presence of a base and in the presence of an organic solvent which is inert under the reaction conditions, in the presence or absence of a phase-transfer catalyst and in the presence or absence of water, at a temperature of 10° to 100° C.

The process thus comprises two different variants. In the first variant, a compound of the formula (IV), in which A is OH, is reacted with a compound of the formula (V), in which B is the previously mentioned leaving group Z (Z=Cl, Br, I or $R^4OSO_2$). According to the second variant, a compound of the formula (IV), in which A is the leaving group Z, is reacted with a compound of the formula (V) in which B is OH.

The flexibility resulting from the two different process variants represents an additional advantage of the process according to the invention, since by this means the number of the starting materials for preparing the bis ethers containing a 2,2'-bis aryl radical is greater than with a single process variant, and in addition, the freedom of choice is provided to seek out, as required, the most readily accessible starting materials for the synthesis.

Therefore, the first variant of the process or the second variant of the process can be preferred respectively as desired, and it should be stated that the two variants are to be considered as equivalent in principle. However, it can be that for purely practical reasons, e.g. ready accessibility of a starting material, in particular the compound of the formula (VI), one of the two variants is preferably used.

In a number of cases it has proved to be useful to use a compound of the formula (IV) in which A is Br. It is also possible to use a compound of the formula (V) in which B is Br.

Usually, the compound of the formula (IV) and the compound of the formula (V) are used in a molar ratio of 1:(2 to 2.2), in particular 1:(2 to 2.1).

The base used is an oxide, hydroxide, carbonate or hydrogen carbonate of an alkali metal or of an alkaline earth metal, a tertiary amine or a mixture of these substances, in particular an alkali metal hydroxide, preferably sodium hydroxide or potassium hydroxide.

Usually, 1 to 2 equivalents of base are used per equivalent of the OH groups present in the compound of the formula (IV) or (V).

The inert organic solvent used can be an aliphatic ketone having 3 to 6 carbon atoms, a cycloaliphatic ketone having 5 to 8 carbon atoms, an aliphatic or cycloaliphatic ether having 4 to 8 carbon atoms, an alkyl nitrile having 1 to 6 carbon atoms in the alkyl radical, a monochlorinated or polychlorinated hydrocarbon having 1 to 6 carbon atoms, a dialkylcarboxamide having 1 to 4 carbon atoms per alkyl group and having 1 to 4 carbon atoms in the acyl radical or a mixture of these substances, in particular acetone, tetrahydrofuran, dioxane, acetonitrile, dichloromethane, chloroform or a mixture of these substances, preferably acetonitrile or dichloromethane.

The procedure can be carried out, as already mentioned, in the presence or absence of a phase-transfer catalyst. The use of a phase-transfer catalyst is advisable if the compounds of the formula (I) are prepared in a system comprising two phases. The phases in this case may be liquid/liquid or liquid/solid.

Phase-transfer catalysts which are suitable are quaternary ammonium or phosphonium salts, for example tetraalkylammonium, tetraphenylammonium, trialkylphenylammonium, tetraalkylphosphonium, tetraphenylphosphonium or trialkylphenylphosphonium salts. The alkyl radicals can be identical or different and generally have 1 to 18, in particular 2 to 16, carbon atoms.

Quaternary ammonium or phosphonium halides have been used very successfully, in particular chlorides or bromides. However, use may also be made of crown ethers, in particular 18-crown-6, as phase-transfer catalyst.

Usually, the phase-transfer catalyst is used in amount of 1 to 10, in particular 2 to 8, mol %, based on the compound of the formula (IV).

If desired, mixtures of the abovementioned phase-transfer catalysts may also be used.

The process may be carried out in a simple manner, without giving rise to significant expenditure on equipment. The individual starting materials can be added in any desired order. At all events, care should be taken to ensure that all reactants are present before the preset reaction temperature is established.

Usually, the compounds of the formulae (IV) and (V) are mixed with the base and, if appropriate, the phase-transfer catalyst, the solvent inert under the reaction conditions is added, and the mixture is heated with stirring to the reaction temperature respectively required.

In a number of cases it is sufficient to allow the reaction to proceed at comparatively low temperatures, for example 15° to 80°, in particular 20° to 50°, C. When relatively unreactive starting materials are used, it is advisable to employ higher temperatures, for example up to 100°, in particular 80° to 100°, C.

In some cases it can be useful to carry out the procedure in the presence of water. Usually, the presence of water is not necessary and the reaction may be allowed to proceed in the absence of water.

However, addition of water is helpful in the work-up of the reaction mixture following the preparation, since, by adding water, undesirable by-products and impurities, for example unreacted base and the salts formed in the reaction, may be removed in a simple manner by extraction.

The process according to the invention may be carried out continuously or batchwise, in particular batchwise. It can be performed at reduced pressure, atmospheric pressure or superatmospheric pressure. Usually, atmospheric pressure is employed.

For the sake of completeness, reference may be made at this point to the fact that a catalyst which contains the compounds of the formula (I) is subject-matter of a German Patent Application (File No. 196 25 168.0–41) filed on the same day as the present patent application.

The examples below describe the invention in more detail without restricting it.

Experimental Part

Example 1

Preparation of 2,2'-bis(phenoxymethyl)-1,1'-binaphthyl

A mixture of 11.0 g (25 mmol) of 2,2'-bis(bromomethyl)-1,1'-binaphthyl, 4.8 g (51.2 mmol) of phenol, 5.0 g (89.3 mmol) of pulverized potassium hydroxide and 1.14 g (5 mmol) of triethylbenzylammonium chloride is admixed with 30 ml of dichloromethane and stirred for 5 hours at 40° C.

The mixture is then extracted twice, each time with 10 ml of water, the aqueous phase is separated off, the organic phase is dried with magnesium sulfate and filtered, and the filtrate is concentrated under reduced pressure.

This produces 11.5 g of a colorless solid which is recrystallized from acetonitrile. This produces 8.8 g of colorless crystals (corresponding to 76% of theory) having a melting point of 117.6° to 118.2° C.

Elemental analysis $C_{34}H_{26}O_2$ (466.6)

Calculated: C 87.5% H 5.6% O 6.9%

Found: C 87.5% H 5.6% O 6.9%

Example 2

Preparation of 2,2'-bis(phenoxymethyl)biphenyl

A mixture of 25.0 g (73.5 mmol) of 2,2'-bis(bromomethyl)biphenyl, 14.2 g (151 mmol) of phenol, 14.7 g (261 mmol) of pulverized potassium hydroxide and 3.41 g (15 mmol) of triethylbenzylammonium chloride is admixed with 120 ml of dichloromethane and stirred for 5 hours at 40° C.

The mixture is then extracted twice, each time with 10 ml of water, the aqueous phase is separated off, the organic phase is dried with magnesium sulfate and filtered, and the filtrate is concentrated under reduced pressure.

This produces 26.8 g of a colorless solid which is recrystallized from acetonitrile. This produces 22.8 g of colorless crystals (corresponding to 85% of theory) having a melting point of 52° C.

Elemental analysis $C_{26}H_{22}O_2$ (366.3)

Calculated: C 85.3% H 6.1% O 8.7%

Found: C 85.2% H 6.1% O 8.7%

We claim:

1. A compound of the formula (I)

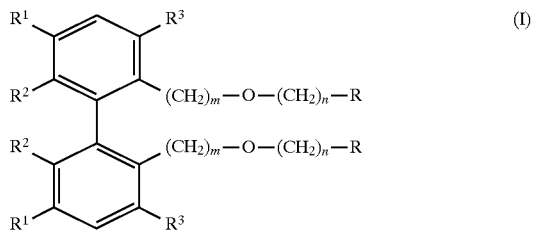

in which $R^1$, $R^2$ and $R^3$ are identical or different and, independently of one another, are hydrogen, an alkyl or alkoxy group having 1 to 4 carbon atoms, an alkenyl group having 2 to 4 carbon atoms, or $R^1$ and $R^2$ including the respective carbon atoms bound to them form a ring containing 6 carbon atoms, m is 1 and n is 0 or 1, and (m+n) is 1 or 2, and R is a phenyl or naphthyl radical which is unsubstituted or substituted by an alkyl group having 1 to 4 carbon atoms or an amino or dialkylamino group containing a total of 2 to 8 carbon atoms.

2. A compound as claimed in claim 1 wherein $R^1$, $R^2$ and $R^3$ are identical or different and independently of one another are hydrogen, an alkyl or alkoxy group having 1 to 2 carbon atoms or $R^1$ and $R^2$ including the respective carbon atoms bound to them form a ring containing 6 carbon atoms.

3. A compound as claimed in claim 1 wherein m=1 and n=0, or m=1 and n=1.

4. A compound as claimed in claim 1 wherein R is a phenyl or naphthyl radical which is unsubstituted or substituted by an alkyl group having 1 to 4 carbon atoms.

5. A compound as claimed in claim 1 wherein R is a phenyl radical which is unsubstituted or substituted by an alkyl group having 1 to 4 carbon atoms.

6. A compound as claimed in claim 1 wherein R is a phenyl radical.

7. A compound as claimed in claim 1 wherein said formula (I) corresponds to the formula (II) or (III)

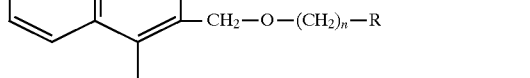

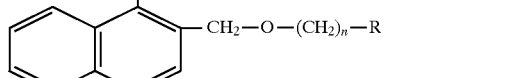

in which n and R have the meaning as defined in claim 1.

8. A process for preparing compounds of the formula (I) as claimed in claim 1, which comprises reacting a compound of the formula (IV)

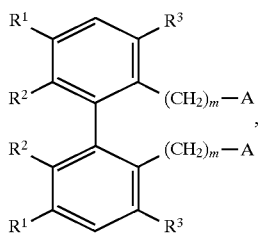

in which $R^1$, $R^2$, $R^3$ and m have the meanings as defined in claim 1 and A is OH or a leaving group Z, where Z is Cl, Br, I or a $R^4OSO_2$ group and $R^4$ is a $CH_3$, phenyl, tolyl or trialkylammonium radical having 1 to 4 carbon atoms per alkyl radical, with a compound of the formula (V)

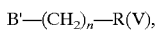

in which R and n have the meaning as defined in claim 1 and B' is the abovementioned leaving group Z if A is OH, or B' is OH if A is the leaving group Z, in a molar ratio of 1:(2 to 2.2) in the presence of a base and in the presence of an organic solvent which is inert under the reaction conditions, in the presence of absence of a phase-transfer catalyst and in the presence or absence of water, at a temperature of 10° to 100° C.

9. The process as claimed in claim 8 wherein a compound of the formula (IV) in which A is Br is reacted.

10. The process as claimed in claim 8 wherein a compound of the formula (V) in which B' is Br is used.

11. The process as claimed in claim 8 wherein the compound of the formula (IV) and the compound of the formula (V) are used in a molar ratio of 1:(2 to 2.2).

12. The process as claimed in claim 8 wherein the base used is an oxide, hydroxide, carbonate or hydrogen carbonate of an alkali metal or an alkaline earth metal, or a tertiary amine or a mixture of these substances.

13. The process as claimed in claim 8 wherein the base used is an alkali metal hydroxide.

14. The process as claimed in claim 8 wherein the base used is sodium hydroxide or potassium hydroxide.

15. The process as claimed in claim 8 wherein 1 to 2 equivalents of base are used per equivalent of the OH groups present in the compound of the formula (IV) or (V).

16. The process as claimed in claim 8 wherein the inert organic solvent used is an aliphatic ketone having 3 to 6 carbon atoms, a cycloaliphatic ketone having 5 to 8 carbon atoms, an aliphatic or cycloaliphatic ether having 4 to 8 carbon atoms, an alkylnitrile having 1 to 6 carbon atoms in the alkyl radical, a monochlorinated or polychlorinated hydrocarbon having 1 to 6 carbon atoms, a dialkylcarboxamide having 1 to 4 carbon atoms per alkyl group and having 1 to 4 carbon atoms in the acyl radical or a mixture of these substances.

17. The process as claimed in claim 8 wherein the inert organic solvent used is acetone, tetrahydrofuran, dioxane, acetonitrile, dichloromethane, chloroform or a mixture of these substances.

18. The process as claimed in claim 8 wherein the organic acetonitrile solvent is or dichloromethane.

19. The process as claimed in claim 8 wherein the phase-transfer catalyst used is a quaternary ammonium or phosphonium salt or a crown ether.

* * * * *